United States Patent [19]

Sullivan et al.

[11] 4,304,997
[45] Dec. 8, 1981

[54] ELECTRON CAPTURE DETECTOR WITH THERMIONIC EMISSION ELECTRON SOURCE

[75] Inventors: James J. Sullivan, Newark, Del.; William P. Kruger, Los Altos Hills, Calif.; Douglass McManigill; Armand P. Neukermans, both of Palo Alto, Calif.

[73] Assignee: Hewlett-Packard Company, Palo Alto, Calif.

[21] Appl. No.: 15,688

[22] Filed: Feb. 27, 1979

[51] Int. Cl.³ .................... H01J 39/28; G01N 27/62
[52] U.S. Cl. .................... 250/379; 250/382; 250/385; 250/389; 324/465; 324/470
[58] Field of Search ............ 73/23.1; 250/379, 375, 250/389, 381, 336, 382, 385; 313/310; 324/33, 465, 470, 469; 315/111.9

[56] References Cited

U.S. PATENT DOCUMENTS

| | | | |
|---|---|---|---|
| 3,134,898 | 5/1964 | Burnell et al. | 250/379 |
| 3,154,680 | 10/1964 | Greene | 250/375 |
| 3,171,028 | 2/1965 | Lovelock | 324/33 |
| 3,361,907 | 1/1968 | Gregory | 324/33 |
| 3,378,725 | 4/1968 | Bochinski et al. | 250/389 |

FOREIGN PATENT DOCUMENTS 375548  3/1973  U.S.S.R. .

OTHER PUBLICATIONS

Braude et al., "Detection of Electronegative Substances in a Unipolar Discharge", Chem. Ab. 80, 33630k, 1974.

Primary Examiner—Alfred E. Smith
Assistant Examiner—Carolyn E. Fields
Attorney, Agent, or Firm—Donald N. Timbie

[57] ABSTRACT

An electron capture detector in which a thermionic source such as a filament provides electrons for the reaction in a source chamber having a port that connects to a detection chamber having a collector. Guard gas is introduced into the source chamber and sample gas into the detection chamber, and an exhaust port is provided in the detection chamber.

23 Claims, 5 Drawing Figures

ELECTRON CAPTURE DETECTOR WITH THERMIONIC EMISSION ELECTRON SOURCE

BACKGROUND OF THE INVENTION

This invention relates generally to ion detectors and more particularly to an electron capture type of detector for use in detecting the constituent gases of a sample eluted from a gas chromatograph.

Ionization detectors for gas chromatography are well known in the art and have been described in the literature. For example, a review of such detectors is contained in an article entitled "Ionization Methods for the Analysis of Gases and Vapors", by J. E. Lovelock, *Analytical Chemistry*, Vol. 33, No. 2, February 1961, pages 162–178. The most commonly used ionization detector in gas chromatography is the radioactive source electron capture detector. This type of detector features high sensitivity and high selectivity towards electrophilic compounds and is widely used for detecting trace amounts of pesticides in biological systems and in food products. Such compounds typically containing halogens combine with free electrons in the detector. The resulting decrease in free electrons is monitored and used as an indication of the concentration of the test substances in a sample.

Traditionally, the free electrons in an electron capture detector are produced by radioactive beta emitters in the form of foils or platings disposed inside the detector. Examples of such beta emitters are Tritium ($H^3$) and Nickel-63 ($Ni^{63}$).

There are disadvantages to the use of radioactive detectors. They may be operated only under license from a Federal and/or state governmental agency. Tritium detectors are prohibited from operating at temperatures above 325° C. to avoid release of radioactivity into the atmosphere. Nickel-63 detectors must undergo periodic wipe tests to insure against radioactive leaks.

An additional disadvantage is that the radioactive beta emitters produce particles having sufficient energy to undesirably polymerize various compounds which may be present in the detector, thus necessitating frequent cleaning of the detector. Also, the energetic radicals created by beta bombardment can create a host of side reactions. Careful operation is often required to maintain operation of the detector in the electron capture mode rather than as a mobility or cross-section detector. Furthermore, in the case of a Nickel-63 detector, the betas emitted have a relatively long range so it is necessary to keep the volume of the detector relatively large, on the order of a milliliter, to avoid undesirable cross-section effects. Such a large volume is a serious drawback which precludes the detector from being used efficiently with capillary columns which elute small gas flows and therefore require a small volume detector.

Still another disadvantage of radioactive detectors is that the free electrons are created from relatively few primary particles. Consequently, the detector has significant shot noise which limits the minimum detectable quantity of a test substance.

Various attempts have been made to overcome the disadvantages of radioactive source electron capture detectors. For example, a radioactive source protected from contamination by use of a scavenging gas has been proposed by N. L. Gregory in the *Journal of Chromatography*, Vol. 13, 1964, pages 26–32. Other researchers have tried to produce free electrons in a detector by use of gaseous corona discharge, radiofrequency discharge, or photoionization techniques. Commercial use of such devices have been found unsatisfactory in electron capture detection because of high noise generation, source instability, lack of detector sensitivity, or a low signal-to-noise ratio.

The use of a non-radioactive, thermionic emitter as the source of free electrons has been proposed by A. K. Braude and V. A. Rotin. The emitter and other detector components are disposed in a common chamber, and a flow of guard gas is intended to reduce the contamination of the emitter by the test substance. The work of Braude and Rotin has been published in *Chemical Abstracts*, Vol. 80, 3363K, 1974, and in U.S.S.R. Pat. No. 375548 issued Mar. 23, 1973.

SUMMARY OF THE INVENTION

The present invention provides an electron capture detector that does not use a radioactive electron source and eliminates its attendant disadvantages such as licensing requirements, contamination, cross-section effects, and noise. The detector of the invention features a thermionic electron source such as a filament that is stable, protected from contamination, and substantially noise free. The detector operates with a sensitivity, large signal-to-noise ratio, and high temperature capabilities comparable to or better than radioactive detectors currently commercially available.

According to the illustrated embodiments of the invention, there are provided an electron source chamber and an adjacent detection chamber in which electron capture takes place. The source chamber contains a thermionic electron emitter, and includes an inlet port and an outlet port or ports for directing an inert guard gas past the emitter. A dense cloud of electrons is established in the source chamber by applying a selected heating voltage to the thermionic emitter and by biasing it negatively with respect to the interior walls of the source chamber.

The detection chamber is disposed to receive free electrons and may also receive a flow of guard gas from the outlet ports of the electron source chamber. The detection chamber has an inlet port for receiving a sample gas as well as an outlet port for exhausting the sample gas and the guard gas. A collector electrode in the detection chamber is biased so as to collect the free electrons in the absence of electrophilic substance. Under appropriate conditions, the presence of electrophilic substances in the detection chamber will reduce the flow of electrons to the collector. The resulting change in current flow to the collector electrode is a measure of the quantity of the electron capturing constituent in the sample gas.

The operating principles of the detector may be explained as follows. Because of the weak electrical field between the output port of the source chamber and the collector, electrons from the cloud within the source chamber proceed through the outlet port of the source chamber into the detection chamber largely by diffusion. Thus, they may be considered as being thermal free electrons. The electrons remain thermal in the detection chamber because of the low field that is generally present there. This is important because it increases the chance that they will become attached to an electrophilic molecule. More importantly, when such attachment occurs, the time for the captured electron to reach the collector is much greater than the time for free electrons to reach the collector owing to the fact that the force on the captured electron must accelerate the relatively heavy molecule to which it is attached. This slowly moving negatively charged molecule within the detection chamber is similar to a negative grid in its action and greatly reduces the number of electrons reaching the collector. Under the above condition where diffusion plays an important role, the sensitivity of such a detector is proportional to the ratio of the average dwell time of the molecules that have captured electrons to the average transit time of the free electrons across the detection chamber.

If the primary source of electrons were located in the detection chamber, as in the prior art, it would be necessary to have a relatively high electric field in order to have appreciable emission. Such a field decreases the probability of electron capture and reduces the grid action of the ions. By placing the electron source in a separate source chamber, the potential difference between the source and the walls of the source chamber can be made as great as is required for efficient electron production without creating fields in the detection chamber. Provision of two chambers, one serving as a means for providing free electrons and the other serving to detect the amount of electrophilic compound present, makes it possible to optimize the design of each.

While the use of guard gas reduces the attack of the filament by gases from the detection chamber, it does not protect common emitters such as used in vacuum tubes or ionization guages. We have found that barium zirconate as described by McNair in *Review of Scientific Instruments*, 38,124 (1967) for use in oxidizing atmospheres works well in the detector. It has also been found that the following materials are acceptable barium aluminate ($BaO-Al_2O_3$), barium silicate ($BaO-2SiO_2$), barium tantalate ($BaO-Ta_2O_5$); barium titanate ($BaO-TiO_2$); barium tungstate ($BaO-WO_3$); and barium vanadate ($2BaO-V_2O_5$). More exactly, the compounds are non-stoichiometric. For instance, barium tungstate would be $(BaO)_n \cdot (WO_3)_{1-n}$ where the index n varies with the particular form of manufacture.

Another advantage of the two chamber detector is that two currents can be monitored, one in the source chamber and one in the detection chamber. Any variation in thermionic emission can therefore be discriminated from signals due to electron capture, which cannot be done if only one current is measured as in a diode.

A further advantage of the detection of this invention is that it can be made of quartz or other inert material whereas prior detectors were made of metal in order to insure against leakage that would release harmful radioactive material. It is also possible to operate the detector at much higher temperatures.

THE DETECTOR

Figures 1, 5:
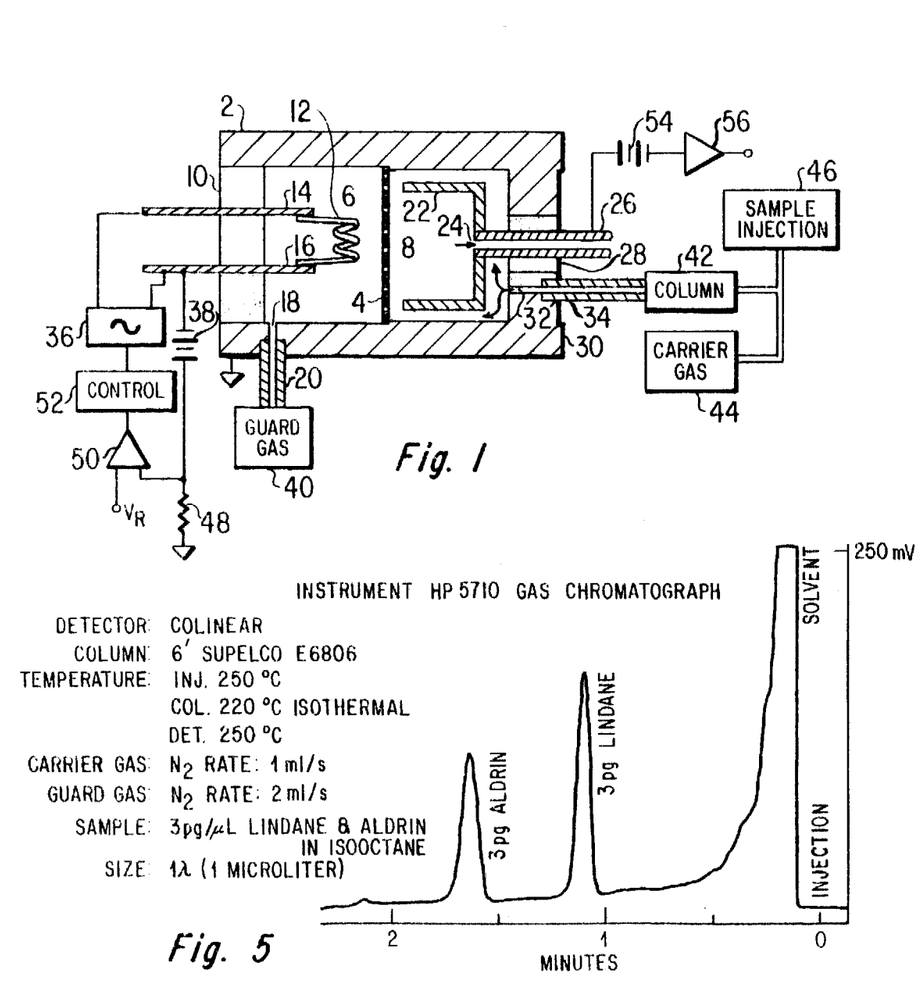
FIG. 1 is a diagramatic cross-sectional view of one embodiment of the present invention.
FIG. 5 is a chromatogram illustrating the operation of the embodiment of the invention shown in FIG. 4 in detecting the pesticides Lindane and Aldrin in a test sample.

Reference is made to the schematic representation of an embodiment of the invention illustrated in FIG. 1. It is comprised of a cylindrical body 2 that may be made entirely of metal or from insulating material lined on the inside with a conductive coating. A perforated plate 4 of conducting material divides the space inside this body 2 into space for a filament chamber and space for a detection chamber. The end of the filament chamber 6 remote from the plate 4 is closed by a cylindrical wafer 10 of insulating material and a filament 12 is mounted between the ends of conductive support rods 14 and 16 that extend through the wafer 10. A port 18 extends through the body 2 at a point near the filament 12 and communicates with a tube 20.

A cup shaped electrode 22 forms a detection chamber 8 with its open end adjacent to the perforated plate 4. A port 24 in the bottom of the cup 22 communicates with a tube 26 of electrically conducting material that extends through an electrically insulating insert 28 mounted in the end wall 30 of the body 2. A port 32 in the end wall 30 communicates with a tube 34 that can be made of conducting or non-conducting material.

ASSOCIATED COMPONENTS

The filament 12 is heated by passing current through it from a floating power source 36 that is connected to the filament support rods 14 and 16. A source 38 of DC bias voltage is connected between the filament support rod 16 and the body 2 so as to make the latter positive with respect to the filament. The bias voltage is of such value as to cause a charge flow of electrons to be generated in the space between the filament 12 and the perforated plate 4 as well as between the filament and the walls. A source 40 of guard gas, which is non-electrophilic and is chemically inert in the environments of the filament chamber 6 and detection chamber 8, is coupled to the tube 20.

Gas to be analyzed such as the elutants from a chromatographic column 42 are conducted to the tube 34 so as to enter the detection chamber 8 via the port 32. The input of the column 42 is supplied with carrier gas from a source 44 and with a sample to be analyzed from a sample injector 46. Guard gas entering the port 18 and the combined carrier and sample gas entering the port 32 are exhausted through the conductor tube 26.

Maintenance of constant emission, while desirable but not completely necessary, may be accomplished by controlling the power supplied to the filament in the general manner shown or by controlling the applied bias voltage of the filament. The body 2 is connected to ground and a resistor 48 is connected in series with the source 38 of bias voltage and ground. One input of a comparator 50 is connected to a point of reference voltage $V_R$ and its other input is connected to the junction of the bias source 38 and the resistor 48. The output of the comparator 50 is applied to control means 52 that operates to change the alternating current voltage supplied by the source 36. When the emission of the filament 12 falls, the voltage across the resistor 48 also falls and the comparator 50 increases the AC voltage supplied by the source 36 via the control 52. The output signal can be detected with at least two modes of operation, constant voltage or constant current.

If the output signal is to be recovered by maintaining a constant voltage across the detection chamber 8, i.e., between the collector 22 and the grounded body 2, the tube 26 is connected to the positive terminal of a battery 54, and the negative terminal of the battery is connected to an electrometer 56. The observed current excursion at the output of the electrometer is a measure of the concentration of the electrophilic substance in the detection chamber 8. Under conditions where a large amount of electrophilic substance is present in the detection chamber 8, the current excursion, normally a decrease, will show saturation.

In order to expand the range of output signal when large amounts of electrophilic compound are present in the detection chamber 8, means are provided for maintaining the current flowing between ground and the collector 22 at a constant value. The output signal then is the voltage excursion required to maintain a constant current. The manner in which this can be done is well known to those skilled in the art.

By making the output port or ports of the source chamber 6 through which the guard gas flows to the detection chamber sufficiently restrictive, the flow of guard gas required to minimize damage to the filament by gases in the detection chamber can be significantly reduced. This is important because too great a flow of guard gas dilutes sample concentration unduly. Whereas, this also reduces the number of electrons that can diffuse through the same port into the detection chamber, the number that do can be sufficient to prevent saturation in the presence of the largest amount of electrophilic compounds that will be encountered in practice.

SECOND EMBODIMENT

Figure 2:
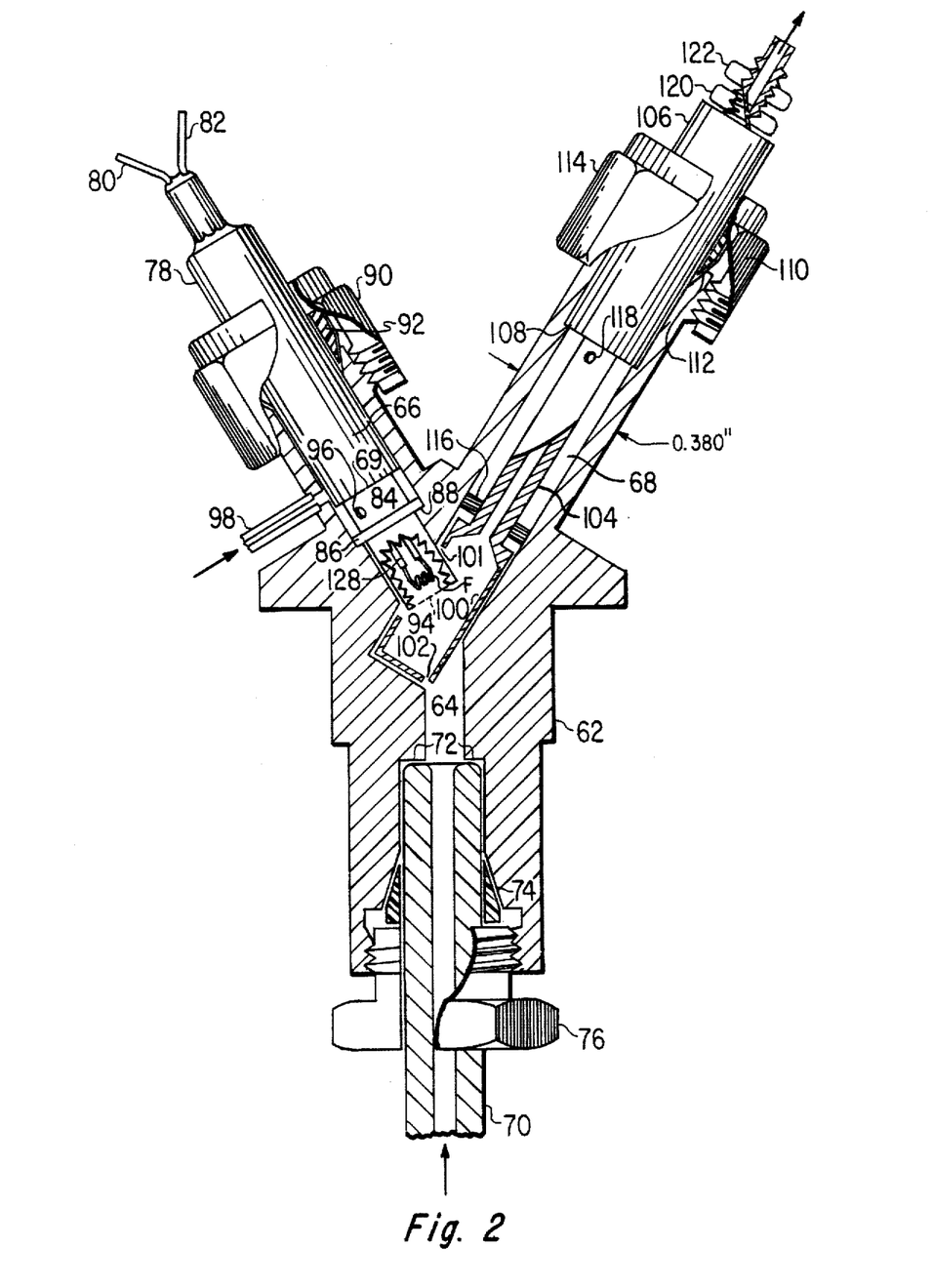
FIG. 2 is a cross-sectional view of another embodiment of the present invention.

In the electron capture detector illustrated in FIG. 2, a metal body 62 is in the form of a Y with longitudinal channels 64, 66 and 68 respectively extending through the stem, left hand and right hand branches. A tube 70 that is to be a chromatographic column or can be coupled to same, extends upwardly into the opening 64 and rests against an annular shoulder 72. An hydraulic seal is provided by compressing an annulus 74 of plastic material that has a wedge shaped cross-section with a nut 76.

The source chamber is inside the inner end of a hollow metal cylinder 78 that is inserted with a loose fit into the longitudinal opening 66. From a point 69 to its outer end, the cylinder 78 is filled with plastic through which stiff electrical conductor 80 and 82 pass. They also pass through a hollow diametrically restricted portion 84 of the cylinder 78 that lies between the point 69 and an annular rim 86. The rim 86 is pressed against an annular shoulder 88 by a nut 90. The nut also compresses a plastic annulus 92 so as to form an hermetic seal. As can be seen through the cut away section at the inner end of the cylinder 78, a filament F is mounted between the ends of the stiff rods 80 and 82, and a screen mesh 94 is mounted across the inner end of the cylinder 78. A hole 96 extends through the wall of the restricted portion 84 of the cylinder 78 and a tube 98 communicates with the longitudinal channel 66. Guard gas introduced into the tube 98 flows along the space between the walls of the opening 66 and the outer surface of the cylinder 78 into the annular space between the restricted section 84 and the walls of the longitudinal channel 66 and then into the cylinder 78 through the hole 96. The guard gas then passes by the filament F and through the screen mesh 94.

The detection chamber lies within a collector cylinder 100, herein shown in solid line rather than cross hatch for the sake of clarity. The collector cylinder 100 is coaxial with the longitudinal channel 68 in the right hand branch of the Y and has an opening 101 which closely surrounds but does not touch the inner end of the cylinder 78 so that the screen mesh 94 lies completely inside the detection chamber. In this way nearly all electrons that diffuse through the screen mesh 94 flow to the collector cylinder 100. The cylinder 100 also has an opening 102 through which elutants from a column coupled to the tube 70 pass into the detection chamber. A tube 104 extends from the cylinder 100 through the outer end of the longitudinal channel 68 in the right branch of the Y. The outer portion of the tube 104 is contained within an insulating plastic filled cylinder 106 having an inner end abutting against an annular shoulder 108. An hermetic seal is formed against the inside of the cylinder 106 by drawing an annular plastic washer 110 having a wedge shaped cross-section inwardly against the outwardly flared surface 112 at the outer end of the longitudinal channel 68 with a nut 114. Although most of the gas passing from a column through the channel 64 will enter the detection chamber within the cylinder 100 via the opening 102, some of it will pass between the outside of the cylinder 100 and the inner surface of the longitudinal channel 68. It may also pass through or past an insulating washer 116 that supports the tube 104 at a point near the outer end of the cylinder 100, and if it does, it will enter the tube 104 via a hole 118. Nuts 120 and 122 serve to connect a lead to means for providing the output signal. The Y body 62 can be connected to ground or some reference potential, and a source of bias voltage can be connected between either of the stiff rods 80 or 82 that support the filament 7 and the body 62 as shown in FIG. 1.

The chromotograms of FIG. 3 were obtained from the detector illustrated in FIG. 2 under the conditions and with the parameters set forth below. The upper trace 124 shows a chromatogram of two test compounds, Lindane and Aldrin, in an iso-octane solvent. Each of the test compounds is present in a quantity of 1.3 picograms. The signal-to-noise ratio for Lindane is about 50, so that the minimum detectable level for this compound is 0.052 picograms. The chromatographic conditions were:

| | |
|---|---|
| Detector temperature | 250° C. |
| Carrier gas | 60ml/min. nitrogen |
| Guard gas | 30ml/min. nitrogen |
| Chromatograph Oven | 180° C. |
| Column | 5% OV-1 stationary phase, coated on 80-100 mesh Chromasorb W-HP support, 4mm internal diameter, 3 feet long. |

The detector conditions were:

| | |
|---|---|
| Filament bias voltage | 38v |
| Filament current | 2A RMS |
| Filament resist. | 1.7 ohms |
| Emission current | 3μA |
| Collector voltage | +.96v |
| Detector chamber volume | 300μ liter |
| Source chamber | 2 mm between filament F and screen mesh 94. |

| | -continued |
|---|---|
| Screen mesh | 25% open<br>hole size .15mm each<br>diameter 4.5 mm |

The lower trace 126 shows a chromatogram run on a commercial radioactive electron capture detector in which the amounts of the compounds are each 1.5 picograms. The signal-to-noise ratio for Lindane is about 33, giving a minimum detectable level of 0.079 picogram. The chromatographic conditions were as follows:

Detector: 15 millicuries of nickel 63, constant current variable pulse frequency type circuitry.
Detector temperature: 250° C.
Carrier gas: 60 ml/min. nitrogen
GC oven: 210° C.
Column, 4 mm internal diameter, 3 feet long, 10% OV-1 stationary phase, Chromasorb G-HP, coated on 80-100 mesh Thus, the nonradioactive detector is equivalent in minimum detectable level to presently known radioactive detectors.

COAXIAL DETECTOR

Figure 4:
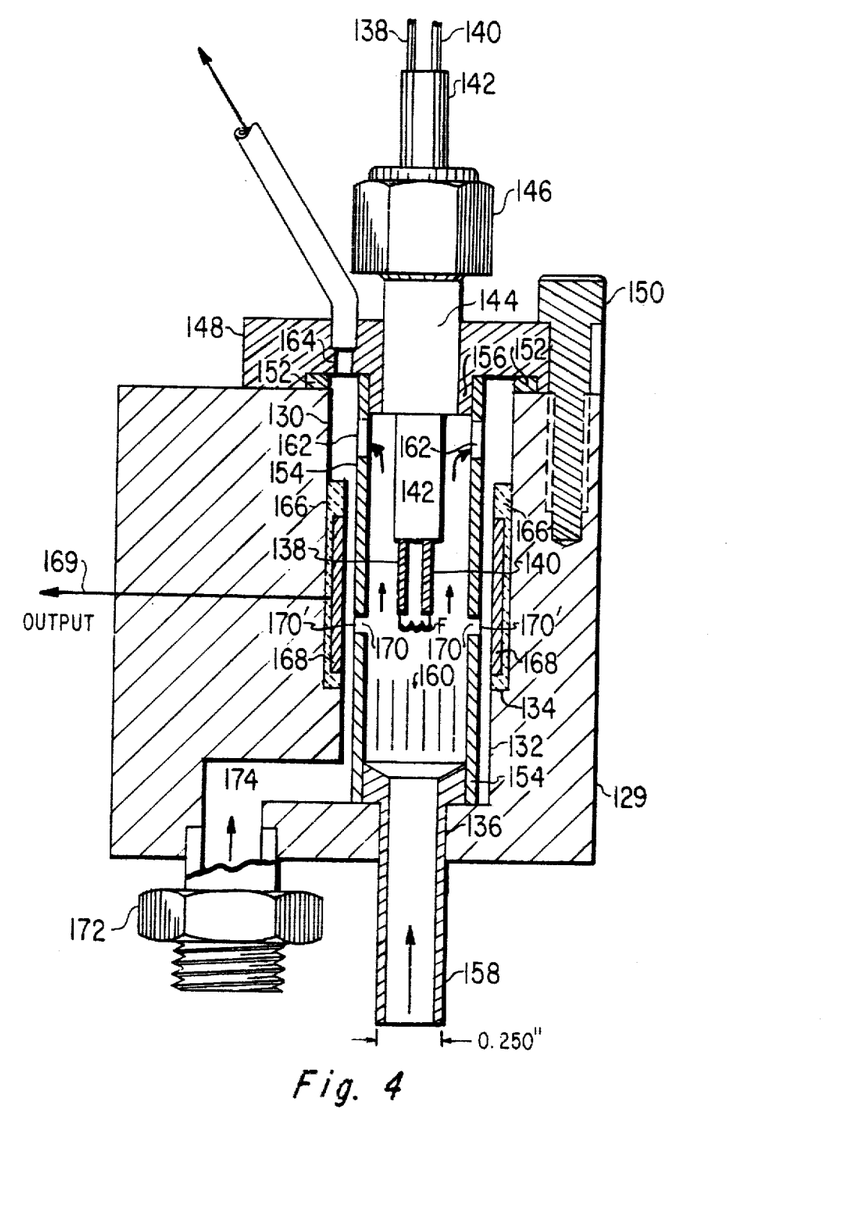
FIG. 4 is a cross-sectional view of an embodiment of the invention utilizing a coaxial flow of sample and guard gas.

In the detector shown in FIG. 4 the guard gas and column or sample gas flow in parallel paths across opposite sides of the screen mesh between the source chamber and the detection chamber with the same velocity so that no pressure differential exists across the mesh. This minimizes the flow of gas from either chamber to the other.

The detector is contained in a metal block 129 that may be temperature controlled by means not shown. A cylindrical cavity 130 is formed in the block 128 and has a section 132 of reduced diameter that forms an annular shoulder 134. The section 132 communicates with a cylindrical passage 136 of still smaller diameter that extends through the bottom of the block 129.

Stiff conductors 138 and 140 are embedded in a solid ceramic cylinder 142 that extends through a metal cylinder 144, the cylinders 142 and 144 being coaxial with the cylindrical cavity 130. Hermetic sealing between the ceramic cylinder 142 and the metal cylinder 144 is provided by compression of an annular plastic wedge, not shown, by a nut 146. These latter components are not shown in cross-section in the interest of clarity. The metal cylinder 144 is brazed to a top plate 148 that is secured to the block 129 by screws such as indicated at 150. Only one screw is shown because of the plane at which the cross-section is taken. A ring seal 152 is compressed between the top plate 148 and the block 129. The ceramic cylinder 142 extends through and below the metal cylinder 144, and the rods 38 and 140 extend still farther into the cavity 130. A filament F is connected across the ends of the rods 138 and 140. One end of a hollow metal cylinder 154 that is coaxial with the cylindrical cavity 130 is press fit around a cylindrical projection 156 that extends from the under side of the top plate 148. The cylinder 154 extends to the bottom of the cavity 130 where it is sealed by brazing to the block 129.

Guard gas from a source not shown is introduced to the detector via a tube 158 that extends through the passageway 136 into the bottom end of the metal cylinder 154. Laminar flow of the guard gas is achieved by closely spaced parallel tubes 160 that are parallel to the axis of the cylindrical cavity 130. The guard gas passes up through the hollow cylinder 130, past the filament F, out through apertures 162 at the upper end of the metal cylinder 154, and into the annular space between the metal cylinder 154 and the wall of the cylindrical cavity 130. It then passes via a passageway 164 through the top plate 148.

An annulus 166 of ceramic insulating material that just fits inside the cylindrical cavity 130 rests on the annular shoulder 134. Mounted on the inside of the ceramic annular 166 is a collector in the form of a ring or coating 168 that is spaced from the outer surface of the metal cylinder 154. An insulated lead 169 extends from the collector 168 to a point outside the block 129 so as to provide the output signal of the detector. Apertures 170 are formed around the circumference of the hollow metal cylinder 154 in a plane at the level of the filament F. A conductive mesh (170') is fitted over the apertures 170 so as to provide both an electric shield and a smooth aerodynamic form to cylinder 154.

Sample gas, such as that eluted from a column, is introduced into the block 129 of the detector via a fitting 172 that communicates with a passageway 174 within the block 129. The passageway 174 communicates with the bottom of the reduced section 132 of the cylindrical cavity 130. The gas then flows upwardly in the annular space between the cylinder 154 and the walls of the cavity 130, between the collector 168 and the cylinder 154, past the apertures 170 and out through the passageway 164. The annular space between the metal cylinder 154 and the wall of the cavity 130 at the reduced section 132 is so thin as to induce laminar flow.

Ideally, the velocity and the pressure of the guard gas flowing past the inside of the aperture 170 should be the same as the velocity and pressure of the sample gas flowing past the outside of aperture 170. In practice, especially when using a mesh over aperture 170, no mixing is observed even with a difference in gas velocities. The filament is preferentially oriented vertically so that the thermal plume created by the heated filament lines up with the guard gas flow. The guard gas minimizes the attack on the filament F of the diffusing samples by sweeping these away vertically, and at the same time, the reaction products, if any, never enter the detection chamber. Inasmuch as the guard gas does not mix with the column gas, as in the other embodiment, it does not dilute the latter and affect sensitivity.

In this embodiment, the source chamber lies within the cylinder 154 and the detection chamber is an annular space lying between the cylinder 154 and the collector 168 between a point just above the aperture 170 and a point just below it.

Reference is made to FIG. 5 which shows a chromatogram resulting from the detection of Lindane and Aldrin, and which contains information about the condition under which the run was made.

PARAMETERS AND COMMENT

Figure 3:
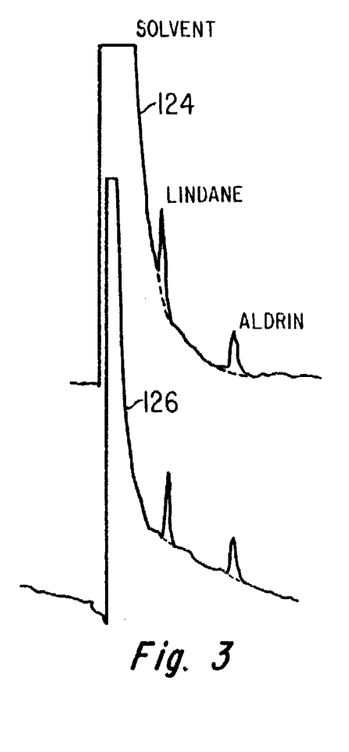
FIG. 3 is a chromatogram illustrating the operation of the present invention in detecting the pesticides Lindane and Aldrin in a test sample.

Although the embodiments of the invention shown in FIGS. 2 and 4 have been drawn to scale and certain operating conditions have been specified in making the chromatograms of FIGS. 3 and 5, it will be understood that variations can be made in dimension and operating conditions within the perview of this invention.

The purpose of the source chamber in any of the embodiments is to provide a copious supply of electrons at the screen mesh or ports between the source chamber and the detection chamber. In order to reduce contamination of the filament by diffusion of gases from the detection chamber to the source chamber, it would be desirable to locate the filament as far from the screen mesh or ports as possible, but the greater this distance is the smaller is the number of electrons that will reach the near side of the mesh. Compensation for this could be made by increasing the temperature of the filament but this shortens its life. In order to attract a greater number of electrons, that are emitted when the temperature of the filament is raised, into the detection chamber 8, the filament would have to be made more negative with respect to the mesh. Accordingly, there are a large number of combinations of filament temperatures, bias voltages and filament locations that could be used.

The walls of the source chamber could be non-conductive, so that the screen mesh itself is the only portion of the source chamber that is positive, but static charges on the surface of the non-conducting surface might have adverse effects or might vary the number of electrons reaching the vicinity of the mesh in an undesirable manner.

It has been found that the detector can still operate to produce useful results if the collection voltage with respect to the screen mesh is increased, but this is generally accompanied by a reduction in sensitivity. This may come about because the electrons move more rapidly to the collector so that there is less likelihood of their becoming attached to an electrophilic particle, or it may be caused by the reduction on the dwell time of the negative ions because they too will move to the collector with greater speed. It might at first seem that the collector would have to be positive with respect to the screen mesh, but it has been found that it may be slightly negative. This is because diffusion is a main driving force on the electrons, and therefore electrons can overcome a small opposing field. Useful results have been attained with voltages ranging from $-0.050$ volts to $+5$ volts.

It would also be possible to construct the detector chamber with non-conductive inner walls, thus leaving the collector as the only metal in the chamber, but once again the charge accumulation on the non-conducting surfaces might cause some undesirable or unpredictable results.

As to the electron source, it is generally desirable to keep the filament temperature as low as possible so as to minimize undesirable side-reactions which always take place with trace amounts of oxygen or water. It is for this reason that a thermionic emitter with very low work function is desired, which, however, also must be stable. As to the position and size of the electron source for maximum sensitivity, it is desirable to react all of the sample gas with the maximum concentration of available electrons. Preferably, no part of the sample gas should be able to flow to the exit hole without being exposed to the flow of electrons. However, it is also understood that the conditions for maximum sensitivity and maximum range of operation are not always compatible.

The electron capture process basically involves a chemical reaction between electrons and an electron capturing species, and therefore to make the reaction proceed as far and as fast as possible, a large electron concentration is desired. Note that in contrast with prior art, the rate of electron generation at the source is practically unlimited. Even if the restriction between the source chamber and detection chamber is quite small, the electron concentration in the detection chamber is quite large and comparable with that existing in the pulsed radioactive detector, even though there is a continuous flow of electrons. If this were done with the radioactive source, the electron concentration would be quite low, because of the limited electron generation rate. The current in the detection chamber is only a small fraction of the current in the source chamber, and so when the current in the detection chamber is reduced by the grid action of the negative ions, the current in the source chamber is barely affected.

Note also that the described negative grid action can exist only when a pure source of electrons can be obtained. With the radioactive detector, the positive space charge of the positive ions inhibits the effect.

We claim:

1. An electron capture detector comprising:
   a first chamber having at least one electrically conductive interior wall;
   a thermionic electron emitter disposed in said first chamber;
   said first chamber having an inlet port and at least one outlet port disposed for conducting a guard gas into and out of said first chamber past said thermionic emitter;
   a first voltage source coupled to said thermionic emitter for heating said emitter;
   a second voltage source coupled between said thermionic emitter and the electrically conductive interior wall of said first chamber for biasing said interior wall positive with respect to said emitter;
   said first and second voltage sources being set to selected voltages to establish an electron cloud having a predetermined high density in said first chamber;
   a second chamber disposed adjacent to said first chamber and in communication with the outlet port of said first chamber for receiving a flow of electrons in said guard gas from said first chamber, said second chamber having an inlet port for receiving a sample gas, and an outlet port for exhausting said sample gas and said guard gas; and
   an electrode disposed in said second chamber for collecting electrons that do not combine with said sample gas.

2. A detector as set forth in claim 1 wherein means are provided for applying a voltage to said electrode for collecting electrons that establishes such a low field in said second chamber that negative ions, when formed, effectively act as a negative grid.

3. An electron capture detecting apparatus, comprising
   means defining a source chamber, at least a portion of the interior surface of said chamber being conductive,
   a thermionic electron emitter mounted in said source chamber,
   an inlet port means for conducting a guard gas into said source chamber,
   outlet port means for conducting guard gas and electrons out of said source chamber,
   a first voltage source coupled to said thermionic emitter for heating said emitter,
   a second voltage source coupled between said thermionic emitter and the electrically conductive portion of said interior surface of said source chamber for biasing said portion of said interior surface positive with respect to said emiter, said first and second voltage sources being such as to establish an electron cloud having a high density in said source chamber, a detection chamber mounted so as to receive a flow of electrons and guard gas from said outlet port means of said source chamber, said detection chamber having an inlet port for receiving a sample gas and an outlet port for exhausting said sample gas and said guard gas, said detection chamber also having electrode means for collecting electrons and negative ions, and means for establishing a voltage between said electrode means and the conductive portion of said inner surface of said source chamber such that said electrode collectors electrons and negative ions in said detection chamber.

4. An electron capture detector, comprising
means defining a hollow source chamber,
thermionic electron emission means mounted so as to supply electrons to said source chamber,
electrode means within said source chamber for collecting electrons,
inlet port means communicating with said source chamber,
outlet port means communicating with said source chamber,
means defining a hollow detection chamber having means defining an opening in communication with said outlet port means of said source chamber, said detection chamber having electrode means for collecting electrons, said latter electrode means being electrically insulated from the electrode means associated with said source chamber,
an inlet port means in said detection chamber, and
an outlet port means in said detection chamber.

5. An electron capture detector as set forth in claim 4 wherein said thermionic electron emission means is comprised of a metal coated with a barium salt.

6. An electron capture detector as set forth in claim 4 wherein means are provided for removably mounting said hollow source chamber.

7. An electron capture detector as set forth in claim 4 wherein said latter outlet port means is in the form of a port communicating with said detection chamber through said electrode means in said detection chamber for collecting electrons.

8. An electron capture detector as set forth in claim 4 wherein said hollow detection chamber is made of conductive material so as to also be the electrode means for collecting electrons, and wherein communication between said detection chamber and said outlet port means of said source chamber is provided by means defining an opening in said detection chamber that is adjacent to and insulated from said outlet port means of said source chamber.

9. An electron capture detector as set forth in claim 4 wherein said outlet port means communicating with said source chamber is comprised of a fine mesh of conductive material.

10. An electron capture detector as set forth in claim 4 wherein said thermionic emission means is a filament and has
means for causing alternating current to flow through said filament,
means for biasing said filament negatively with respect to said electrode means associated with said source chamber for collecting electrons, and means for biasing said electrode means for collecting electrons in said detection chamber positive with respect to said electrode means associated with said source chamber.

11. An electron capture detector as set forth in claim 4 wherein said thermionic electron emitter is comprised of a conductor coated with mixed metal oxides of low work function.

12. An electron capture detector as set forth in claim 4 wherein said thermionic electron emitter is comprised of a conductor coated with one of barium aluminate, barium zirconate, barium silicate, barium tantalate, barium titanate, barium tungstate, and barium vanadate.

13. An electron capture detector as set forth in claim 4 wherein said outlet port means of said source chamber is conductive.

14. An electron capture detector as set forth in claim 4 wherein said outlet port means of said source chamber lies within said detection chamber.

15. An electron capture detector as set forth in claim 4 wherein said means defining a source chamber includes a first hollow member disposed along a first axis, said inlet port means for said source chamber includes a means defining an opening in a side of said first hollow member, said outlet port means of said source chamber being located at one end of said first hollow member and transverse to said first axis, said means defining a detection chamber includes a second hollow member disposed along a second axis that is at an angle other than zero degrees with respect to said first axis, means defining an opening in the side of said second hollow member, means mounting said first hollow member with the end containing said outlet port means adjacent to the opening in the side of said second hollow member.

16. An electron capture detector, comprising
a body of metal having first, second and third intersecting channels therein,
a first assembly removably mounted in said first channel,
means defining a source chamber at the inner end of said assembly,
a filament mounted in said source chamber,
leads connected to said filament insulated from and extending through said first assembly,
means defining an input port in said source chamber,
means defining a passageway in said body that communicates from outside of said body to said input port,
an outlet port for said source chamber comprised of a mesh of conductive material mounted at the inner end of said source chamber,
a second assembly removably mounted in said second channel having
means defining a detection chamber at the inner end of said second assembly,
a collection electrode formed by at least a portion of the inner surface of said detection chamber being conductive,
a tube communicating with said detection chamber so as to form an outlet port therefrom, said tube forming an electrical connection to the said conductive surface,
means for electrically insulating said tube and said collector from said body of metal,
means defining an opening in said detection chamber that communicates with said outlet port of said source chamber in such manner that said collection electrode is electrically insulated from the conductive mesh and from said source chamber, and means defining an inlet port in said detection chamber that communicates with said third channel in said body.

17. A combination for use with an electron capture detector, comprising a source chamber, a detection chamber, an inlet port in said source chamber for the purpose of conducting guard gas into said chamber, an outlet port in said source chamber communicating with said detection chamber, an inlet port in said detection chamber through which matter to be analyzed may be introduced into said detection chamber, an outlet port means for permitting gas to escape from said source and said detection chambers, a thermionic source of electrons mounted so as to be able to supply electrons to said source chamber when suitably energized, electrode means in said source chamber for collecting electrons, when present therein, and for attracting them to a point near the outlet port of said source chamber when a suitable voltage is applied between said electrode means and said thermionic source, and a collector electrode means in said detection chamber for collecting, when a suitable voltage is applied thereto, negatively charged particles when present in the detection chamber.

18. An electron capture detector including the combination as set forth in claim 17 and having means for energizing said thermionic source of electrons, means for applying a direct current voltage between said thermionic source and said electrode means in said source chamber, means for applying a direct current voltage between said collector electrode in said detection chamber and said electrode means in said source chamber, and means for producing a signal indicative of the current flowing through said collector electrode.

19. An electron capture detector as set forth in claim 18 having means for setting the rate at which energy is supplied to said thermionic source, and means for setting said direct current voltages at such values that the charge carried by the flow of electrons from said thermionic source to the electrode means in said source chamber exceeds the charge carried to said collector electrode means in said detection chamber.

20. An electron capture detector as set forth in claim 18 having means for setting the rate at which energy is supplied to said thermionic source, and means for setting said direct current voltages such that negatively charged particles diffuse from said source chamber into said detection chamber.

21. Apparatus for use in an electron capture detector comprising a source chamber, a detection chamber, a port in said source chamber to which a source of gas may be coupled, a port in said detection chamber to which the output of a chromatographic column may be coupled, means permitting gas to flow out of said chambers, a collector electrode in said detection chamber, port means providing for passage of electrons from said source chamber to said detection chamber, means for establishing a first electrical field within said source chamber of such direction as to urge electrons, when present, toward said port means providing for passage of electrons from said source chamber to said detection chamber, means for establishing a second electrical field between said collector electrode and said port means providing for passage of electrons from said source chamber to said detection chamber, a thermionic source of electrons mounted so as to supply electrons to said source chamber, said means for establishing said second electrical field in said detection chamber being such that said second electrical field is sufficiently weak to permit electrons to flow through said port means providing for passage of electrons from said source chamber to said detection chamber largely by diffusion whereby the electrons in said detection chamber are thermal and the sensitivity of the detector with which the apparatus is used is increased in proportion to the approximate rotio of the dwell time in said detection chamber of negative ions produced by interaction between the thermal electrons and electrophilic molecules introduced into said detection chamber and the transit time of electrons between said collector electrode and said port means providing for passage of electrons from said source chamber to said detection chamber.

22. Apparatus as set forth in claim 21 further characterized by means responsive to the current flowing through said first electrical field for maintaining the emission of said thermionic source of electrons at a constant value.

23. Apparatus for use in an electron capture detector, comprising a source chamber having an inlet port through which gas may be introduced into said source chamber, a detection chamber having an inlet port through which gas to be analyzed may be introduced into said detection chamber, a collector contained within said detection chamber, outlet port means for said source chamber coupled to said detection chamber, port means for permitting gas to escape from said source and detection chambers, thermionic emitter means and means for collecting electrons for creating a cloud of electrons at a point in said source chamber adjacent said outlet port means, said cloud being sufficiently dense to cause some of the electrons in said cloud to diffuse through said outlet port means into said detection chamber, and means for establishing said collector electrode at a potential such as to establish a field between the outlet port means of said source chamber and said collector electrode to permit electrons to enter said detection chamber via said outlet port means largely by diffusion.

* * * * *